United States Patent [19]

Messenger et al.

[11] 4,299,740
[45] Nov. 10, 1981

[54] CONCENTRATED ORGANIC SULPHONATE SOLUTIONS

[76] Inventors: Edward Messenger, Ramsey House, Camerton, Workington, Cumbria; Douglas E. Mather, 35, Woodland Ave., Hillcrest; Brinley M. Phillips, 15, Greenlands Ave., both of Whitehaven, Cumbria, all of England

[21] Appl. No.: 165,097

[22] Filed: Jul. 1, 1980

Related U.S. Application Data

[63] Continuation of Ser. No. 56,958, Jul. 12, 1979, abandoned, which is a continuation of Ser. No. 902,424, May 3, 1978, abandoned, which is a continuation of Ser. No. 759,180, Jan. 13, 1977, abandoned, which is a continuation of Ser. No. 648,086, Jan. 12, 1976, abandoned.

[30] Foreign Application Priority Data

Jan. 15, 1975 [GB] United Kingdom ................. 1745/75

[51] Int. Cl.$^3$ ................. C07C 143/02; C07C 143/10; C07C 143/16; C11D 1/14
[52] U.S. Cl. .................................... 252/545; 252/173; 252/523; 252/526; 252/536; 252/541; 252/555; 260/501.21; 260/513 R; 260/513 N; 260/513 T

[58] Field of Search ............... 252/173, 523, 526, 536, 252/541, 545, 555; 260/501.21, 513 R, 513 N, 513 T

[56] References Cited

U.S. PATENT DOCUMENTS

| | | | |
|---|---|---|---|
| 3,332,880 | 7/1967 | Kessler | 252/555 |
| 3,420,875 | 1/1969 | Di Salvo | 260/513 T |
| 3,641,131 | 2/1972 | Marquis | 260/513 T |
| 3,954,679 | 5/1976 | Wixon | 252/555 |
| 4,003,857 | 1/1977 | Gorsich | 252/555 |

*Primary Examiner*—Dennis L. Albrecht
*Attorney, Agent, or Firm*—Frishauf, Holtz, Goodman & Woodward

[57] ABSTRACT

It is known to prepare olefin sulphonates by neutralizing olefin sulphonation products with dilute aqueous bases. This invention provides a method of preparing more concentrated solutions of certain olefin sulphonates by determining the position of the viscosity minimum which occurs at concentrations above the critical limit where gel formation is normally observed and which corresponds to the formation of a 'G' phase, and reacting the olefin sulphonation product with the base in the presence of sufficient water to provide a product having a concentration corresponding substantially to this minimum.

14 Claims, No Drawings

CONCENTRATED ORGANIC SULPHONATE SOLUTIONS

This is a continuation of application Ser. No. 56,958, filed July 12, 1979 abandoned, which in turn, is a continuation of Ser. No. 902,424 filed May 3, 1978 (now abandoned), which is a continuation of Ser. No. 759,180 filed Jan. 13, 1977 now abandoned, which is a continuation of Ser. No. 648,086 filed Jan. 12, 1976 (now abandoned).

The present invention relates to the manufacture of olefin sulphonates in highly concentrated aqueous solutions.

Hitherto olefin sulphonates for use as surfactants have been prepared by neutralising olefin sulphonic acids with dilute aqueous bases. Typically the sulphonic acid is obtained by reacting an olefin with a sulphonating reagent such as $SO_3$ or $ClSO_3H$ to form sulphonation products containing mainly sultones and sulphonic acids and subsequently hydrolysing the sultones, the product being neutralised with a dilute base before, after or during the hydrolysing step. The product of the neutralisation is a mixture, in approximately equal proportions, of alkene sulphonates and hydroxy alkane sulphonates, present as a dilute aqueous solution. The term "olefin sulphonate" is used in the art and in this specification to describe the mixture of sulphonates which is obtained by hydrolysing and neutralising the product of sulphonation of an olefin. According to the conditions of hydrolysis the proportion of alkene sulphonate may vary, but generally lies between about 40 and about 60% by weight of the total sulphonated material. It has been found essential, hitherto, to use dilute bases for the neutralisation because the viscosity of aqueous solutions of the sulphonates has been observed to increase sharply with increasing concentrations until a concentration is reached at which the product becomes too viscous to handle and forms a gel. This concentration depends on the material, and is usually in the region of 30 to 45%.

For this reason olefin sulphonates have hitherto been prepared only in dilute solutions, despite the obvious disadvantages of such solutions for the purposes of storage and transport. It has generally been considered impossible to make the sulphonates above a critical concentration which varies according to the material, but in a typical case (e.g. $C_{16\ to\ 18}$) to about 30 to 45%.

It is possible to increase the concentration of active ingredient by addition of viscosity modifiers or cosolvents, such as alcohols, which act as thinners, both lowering the viscosity of the solution and inhibiting the formation of gels, so that higher concentrations may be attained. Such cosolvents are normally only effective in producing substantial increases in the attainable concentration when they are present in such large amounts that they constitute a fire hazard and adversely affect the properties of the product for many of its desired end uses. The viscosity of the product is also affected by the presence of electrolytes, such as sodium sulphate which is usually present as an impurity formed during manufacture. Electrolytes tend to thicken dilute aqueous solutions of olefin sulphonate, raising their viscosity, and have for this reason been considered undesirable, but they also inhibit gel formation, so enabling pumpable, but undesirably viscous solutions of olefin sulphonate to be obtained at slightly higher concentrations, e.g. up to 50%, than are attainable with the purer materials.

It has been reported (see for example "Advances in Colloid Interface Science" 1 (1967; pp. 82–83) that some detergent compounds are capable of forming liquid crystal phases, including a phase of relatively low viscosity compared with the other liquid crystal phases which is usually referred to as the "G" or "lamellar phase" and which forms only at certain specific high concentrations. However, in most instances, including the case of virtually all those compounds which are of industrial interest, where the existence of a "G" phase has been reported, it can only be formed at elevated temperatures. Thus, for example, sodium lauryl sulphate has been reported to form a "G" phase, at about 74° C., which is pourable. However, due to the elevated temperature required, this phenomenon has hitherto been regarded as having purely academic interest. It has never been possible to apply it in industry.

Neither alkene sulphonates nor hydroxy alkane sulphonates are known to form a "G" phase, nor has it previously been reported that mixtures of different types of detergent compound can exhibit such a phase.

Surprisingly, however, we have now discovered that if the concentration of certain olefin sulphonates is increased from about 40% to about 90%, the viscosity, after initially rising, so that the product sets into gel, then decreases sharply in the region of 55–85% until a point is reached at which the solution is sufficiently fluid to be readily handled. We believe that this phenomenon is due to the formation of a "G" phase by the mixture of alkene sulphonate and hydroxyalkane sulphonate. However, the fluid phase forms at substantially lower temperatures than those usually required to form a "G" phase, with, for example, sodium alkyl sulphates, and it is even possible to obtain it at ambient temperature.

With further increase in concentration the viscosity passes through a minimum and increases sharply, so that the solution again sets into a gel, or similar non-pourable state. Surprisingly we have found that we can apply this phenomenon to the manufacture of olefin sulphonate products at a concentration not hitherto obtainable. This may be achieved moreover in the absence of any cosolvents or similarly harmful and unwanted additives. These desirable products may be produced by neutralising the sulphonic acid with an aqueous base of the required concentration to give a product within the fluid region.

The concentration at which the minimum occurs varies according to the particular sulphonate, its composition and its purity. Variations in composition such as isomer distribution, the relative proportion of alkene sulphonates and alkyl hydroxy sulphonates, and the presence of impurities e.g. unsulphonated hydrocarbon, disulphonates or excess sulphate ion, tends to alter the position of the minimum.

The pourable fluid, containing olefin sulphonates at a concentration substantially above the critical limit at which gel formation is first observed is referred to herein as the "G" phase, it is generally in the form of a viscous liquid or pourable, soft paste.

Our invention provides a method for the preparation of olefin sulphonates which comprises reacting a product of sulphonation of an olefin having an average of up to 20 carbon atoms with a base selected from the group consisting of sodium hydroxide, potassium hydroxide, sodium carbonate, potassium carbonate, ammonia, ammonium carbonate and primary, secondary and tertiary amines having a total of up to 4 carbon atoms, in the presence of sufficient water to give an olefin sulphonate product in the "G" phase.

Preferably the olefin sulphonation product is a sulphonation produce of an olefin, which is hydrolysed prior to or concurrently with the neutralisation. It is also possible to carry out the neutralisation in two stages, by neutralising the sulphonic acid content of the sulphonation product, at least partially hydrolysing the sultones and completing the neutralisation of the hydrolysed material.

The sulphonation product may be obtained from the sulphonation of an olefin having an average of from 8 to 20 carbon atoms, e.g. 12 to 18 carbon atoms, preferably 14 to 18 carbons, and one or more olefinic bonds. Preferably the olefins have a single bond in the $\alpha$ position. For example a sulphonated mixture of $C_{14}$ or $C_{16-18}$ linear $\alpha$ olefins may be used.

The base may be an alkali such as sodium, potassium or ammonium hydroxide or carbonate or an amine having up to six carbons, e.g. methylamine, ethylamine, propylamine, dimethylamine, methyl ethylamine, diethylamine, trimethylamine, triethylamine, or an alkylolamine, such as monoethanolamine, diethanolamine or triethanolamine. Mixtures of the foregoing bases may be employed.

The base is typically employed as an aqueous solution whose concentration depends on the amount of water required to form the product in the "G" phase. The appropriate concentration in any particular instance may be determined for example by running a series of test preparations and a graph of viscosity against concentration may then be plotted in order to locate the position of the minimum. In the event that a concentrated pourable "G" phase is not detected at ambient temperature, the viscosities of the samples may be redetermined at successively elevated temperatures until the viscosity minimum has been located. The minimum occurs generally at a concentration between 60 and 90% weight of active ingredient, usually between 65 and 85%. Typically a pourable "G" phase is obtained at concentrations within about ±5% of the value corresponding to the viscosity minimum. This range varies to some extent according to the material, and may sometimes be slightly widened at elevated temperatures.

The minimum temperature at which the fluid "G" phase occurs varies somewhat according to the nature and purity of the product. Generally, the "G" phase is readily achieved at ambient temperature in the presence of normal levels of manufacturing impurities, and in particular of electrolyte, e.g. sulphate ion in the proportion of about 2.5 to 5% by weight which is usually obtained using commercially sulphonated olefins. The minimum temperature may be rather higher in the case of very pure products, which may in some cases require gentle warming to form the fluid state. Alternativly, minor proportions, e.g. up to about 8% of electrolyte may be deliberately added in order to provide a "G" phase at room temperature or below. Such additions are not generally harmful in the same way as cosolvents.

In the art, and in this specification, the term "electrolyte" is used to describe the non-colloidal ionic impurities which are normally present in solution in the product Usually the electrolyte consists essentially of the sulphate salt of the base used to neutralise the sulphonic acid. However, where electrolyte is deliberately added to the composition in order to obtain a "G" phase at lower temperatures, it will be apparent to those skilled in the art that an equivalent effect may be obtained using any non-colloidal salt which is soluble in the product to the extent required, and which provides ions in solution. In this context "non-colloidal" means not belongign to the class of colloidal electrolytes as described, for example, in S. Gladstone; "Textbook of Physical Chemistry" (1940) P. 1240. Colloidal electrolytes include soaps and anionic detergents. They are characterised by the possession of an ionisable group attached to a high molecular weight organic residue and by their tendency to form colloidal micelles leading inter alia to apparent osmotic pressure anomalies. Obviously some non-colloidal salts will be less suitable than others, e.g. on grounds of chemical instability in the system, toxicity, cost or availability. Typical examples of salts which may be employed include inorganic salts such as the sulphates, chlorides, iodides, bromides, nitrates and phosphates of the alkali metals (e.g. Lithium sodium or potassium) or of ammonium, non-colloidal soluble salts of the foregoing anions with organic bases such as amines and similar salts of organic acids such as the lower carboxylic acids, e.g. ionic, watersoluble, noncolloidal citrates, acetates, formates, tartrates, succinates, fumarates, glycolates, oxalates and the like. Among preferred salts for addition to our compositions there may be mentioned particularly sodium sulphate, sodium chloride and sodium citrate.

It is possible, though less preferred, to lower the minimum temperature of the "G" phase by addition of a cosolvent or viscosity modifier if desired, in order to improve fluidity, for example in cold climates.

All products covered in this specification can be made commercially in a "G" phase at ambient temperatures, either directly or with the addition of small amounts of electrolyte. In this they differ from typical industrial detergents such as sodium alkyl sulphates. Generally, fluid phases are more readily obtained at ambient temperature with ammonia and the lower molecular weight amines (e.g. 1 to 4 carbon atoms) than with sodium or the higher molecular weight amines. The former are generally obtainable in a fluid condition at temperatures below 20° C. even in a relatively pure state while the latter form the fluid phase at room room temperatures when prepared from usual commercial sulphonated olefins, or lower on addition of about 2.4 to 5% electrolyte, or at temperatures up to about 40° C. when prepared from purer feedstocks, in the absence of any such addition.

The amount of base is chosen to provide a product having the desired pH. Usually the desired pH is substantially neutral, but greater or smaller amounts of base may be used if desired, e.g. sufficient to provide a pH between 6.5 and 8.5. Higher pH is possible but usually undesirable, commercially, since it results in produces that are too caustic for many of the most common end uses of olefin sulphonates.

The product of sulphonation of olefins usually contains certain intermediate products, such as sultones which may be hydrolysed by heating in the presence of water and under acidic, neutral or basic conditions.

A preferred manner of carrying out our invention is to mix the product of an olefin sulphonation with an aqueous base, at a concentration required to give a final product in the "G" phase, such that the base is present in sufficient quantity to neutralise the acid components and to hydrolyse and neutralise the sultones and other sulphonate esters. The material is then submitted to conditions of elevated temperatures for an appropriate time to afford hydrolysis of the sultones and other sulphonate esters, preferably 100° to 200° C. for 30 minutes to about 10 hours, e.g. 1 to 8 hours, longer times being required to complete the hydrolysis at lower temperatures.

However, the neutralised but unhydrolysed intermediate is often a viscous paste which is difficult to handle. In such instances it is preferred to combine the neutralisation and hydrolysis steps in a single stage, feeding the acid and base to a neutraliser-hydrolyser vessel maintained at a temperature sufficiently elevated to effect hydrolysis (e.g. about 150° C.). The vessel is preferably stirred.

The invention makes it possible to prepare olefin sulphonates as a concentrated aqueous solution, about twice as concentrated as the corresponding prior art commercial olefin sulphonates, without the need to include viscosity modifying agents such as cosolvents. Such cosolvents, typically lower alcohols, are undesirable in that they may adversely affect the properties of formulations including the olefin sulphonates. They may also present a fire hazard and impart an undesirable odour to the product. We therefore prefer that in our invention cosolvents and viscosity modifiers should be absent, or, if present should only be used in the minor amounts which may be desirable e.g. to ensure fluidity at unusually low temperatures.

In addition to electrolyte and any unhydrolysed sultones, the products of our invention usually contain other common manufacturing impurities such as disulphonates and neutral oil, which comprises unsulphonated olefins, parafins present as imputities in the feedstock, and other non-acid organic material present in the olefin sulphonation product.

The invention is illustrated in the following Examples 1 to 9. All percentages are by weight unless otherwise stated.

EXAMPLE 1

A $C_{14-16}$ alpha olefin obtained by the polymerisation of ethylene by a Ziegler Process and having a mean molecular weight of 205 was sulphonated using a laboratory falling-film reactor at about 35° C. and using 120 molar percent $SO_3$. The $SO_3$ was employed as a gaseous mixture of 2.5 volume/volume percent in air. The intermediate acid product from the reactor, after separaton from the effluent gasses, was matured in an aging vessel at 35° C. for a mean time of five minutes, before being added to aqueous sodium hydroxide.

0.6 moles of the sulphonated olefin product was added to 27.8 g sodium hydroxide dissolved in 40 g water. This hyperalkalised material was then heated in an autoclave at 150° C. for 30 minutes.

The final product was a pourable liquid at temperatures greater than 30° C. and contained 75.1% surface active ingredient, 1.33% neutral oil, and 0.97% sodium sulphate.

EXAMPLE 2

Example 1 was repeated several times using different quantities of water in the aqueous sodium hydroxide to give products of various concentrations.

At 40° those products having active ingredient contents of between 43 and 65% were stiff non-pourable gels whereas those products having active ingredient contents of between 69 and 78% were pourable liquids, the viscosity minimum being at 74.5% active ingredients.

EXAMPLE 3

To demonstrate the effect of commercial impurities the laboratory preparation of Example 1 was repeated on plant scale using a commercial multistage $SO_3$/air sulphonator of the type described in B. Pat. No. 969,517. The product was fluid at ambient temperature (23° C.) at a concentration of 68% by weight and contained 2.8% neutral oil and 2.5% sodium sulphate.

EXAMPLE 4

To illustrate the effect of variation in the composition of the olefin sulphonation product with respect to quantity and isomer distribution of the sultones present, Example 2 was repeated except that the intermediate acid product was matured at 35° C. for 22 minutes, before being added to the aqueous sodium hydroxide.

In this case, at 40° C., the viscosity minimum of the concentrated fluid state occurred at about 78% active ingredient, the product containing 1.33% neutral oil, and 1.02% sodium sulphate.

EXAMPLE 5

To illustrate the effect of varying the disulphonate content of the olefin sulphonation product, Example 2 was repeated using 130 molar percent $SO_3$.

In this case, at 40° C. the viscosity minimum of the concentrated fluid state occurred at about 75% active ingredient, the product containing 0.83% neutral oil, and 1.25% sodium sulphate.

EXAMPLE 6

Example 1 was repeated using a $C_{16-18}$ alpha olefin obtained by the polymerisation of ethylene by a Ziegler Process and having a mean molecular weight of 236 and using 27.8 g sodium hydroxide dissolved in 50 g water in the hyperalkalisation step.

The final product was a soft pourable paste at temperatures greater than 42° C., having an active ingredient content of 74.3%, a neutral oil (i.e. unsulphonated olefin) content of 1.41%, and a sodium sulphate content of 0.9%.

EXAMPLE 7

Example 1was repeated using a $C_{14-18}$ random olefin obtained by dimersation and randomisation of short chain Ziegler olefins, and sulphonated on a plant scale. The olefin had a mean molecular weight of 209. In this example 27.8 g sodium hydroxide dissolved in 63 g water was used in the hyperalkalisation step.

The final product was a pourable liquid at temperatures greater than 18° C., having an active ingredient of 69.3%, a neutral oil content of 2.6%, and a sodium sulphate content of 3.2%.

EXAMPLE 8

Example 1 was repeated using 103.6 g triethanolamine and 50 g water in the hyperalkalisation step.

The final product was a soft pourable paste at temperatures greater than 60° C. having an active ingredient of 79%, a neutral oil content of 1.1%, and a sulphate ion content of 1.0%.

EXAMPLE 9

Example 1 was repeated using 11.8 gm ammonia and 65 gm water in the hyperalkalisation step. The final product remained a pourable liquid when cooled to 0°

C. It contained 67.5% active ingredient, 2.5% neutral oil, and 1.5% sulphate ion.

We claim:

1. In the method for preparing pourable aqueous olefin sulphonate compositions which exhibit an immobile gel phase in at least part of the concentration range 40 to 55% by weight active, and a mobil "G" phase at an active concentration greater than that at which said immobile gel phase is formed, which method consists essentially in reacting sulphonated olefins having from 8 to 20 carbon atoms with a base selected from the group consisting of sodium hydroxide, potassium hydroxide, sodium carbonate, potassium carbonate, ammonia, ammonium carbonate and primary, secondary and tertiary amines having a total of up to 4 carbon atoms, in the presence of water thereby forming an aqueous solution of olefin sulphonate salt containing up to 8% of electrolyte formed as a by-product of said neutralization, the improvement which consists in performing the reaction in the presence of sufficient water to provide an olefin sulphonate product having a concentration corresponding substantially to the minimum value in its concentration against viscosity curve, which occurs between 60 and 90% by weight and above the lowest concentration at which gel formation is observed and in the substantial absence of organic cosolvents or added electrolyte.

2. The method of claim 1 performed in the substantial absence of cosolvent and containing up to 5% of said electrolyte.

3. The method of claim 1 wherein the base is an alkylolamine.

4. A method according to claim 1 which comprises performing in any order the steps of (a) mixing the sulphonated olefin with sufficient of the base to provide a final product of about neutral pH and (b) hydrolysing the sulphonation product with water at between about 100° C. and about 200° C.

5. A method according to claim 4 wherein the olefin has an average of from 12 to 18 carbon atoms.

6. A method according to claim 5 wherein the olefin has 1 ethylenic double bond.

7. A method according to claim 6 wherein the olefin is a straight chain alpha olefin.

8. In the method of preparing pourable aqueous olefin sulphonate compositions which consists essentially in sulphonating an olefin having from 12 to 18 carbon atoms and performing in any order the steps of (a) mixing the sulphonated olefin with aqueous sodium hydroxide to provide about neutral pH and (b) hydrolysing the sulphonation product with water, thereby forming an aqueous solution of sodium olefin sulphonate containing about 2.5 to about 8% of sulphate formed as a by-product of said neutralisation, the improvement which consists in performing at least said step (a) in the presence of only sufficient water to provide the olefin sulphonate product as a pourable aqueous "G" phase with concentration between 60 and 90% by weight of active ingredient and in the substantial absence of organic cosolvents or added electrolyte.

9. A pourable aqueous olefin sulphonate composition consisting essentially of (a) water; (b) between 60 and 90% based on the weight of the composition of an active ingredient which is a mixture of an alkene sulphonate salt with from 40 to 60%, based on the weight of the active ingredient, of a hydroxy alkane sulphonate salt, wherein said salts each comprise an anion having an average of from 8 to 20 carbon atoms and a cation selected from the group consisting of sodium, potassium, ammonium and amines having up to four carbon atoms, and (c) up to about 8% total, based on the weight of the composition of a sulphate of said cation formed as a by-product of a neutralization operation during the production of said sulphate composition and in the substantial absence of organic cosolvents or added eletrolyte, wherein said active ingredient is present as a "G" phase thereby providing a pourable composition.

10. A composition according to claim 9 substantially free from cosolvents wherein said cation is sodium and the component (c) is present in proportion of up to 5% by weight of the composition.

11. A composition according to claim 9, substantially free from cosolvents, wherein said cation is ammonia and the component (c) is present in proportion of up to 5% by weight of the composition.

12. A composition according to claim 9, substantially free from cosolvents, wherein said cation is an amine having from 1 to 4 carbon atoms and the component (c) is present in proportion of up to 5% by weight of the composition.

13. A composition according to claim 12 wherein said cation is an ethanolamine having from 1 to 2 hydroxyethyl groups.

14. A pourable aqueous olefin sulphonate composition consisting essentially of (a) water; (b) from 60 to 80% by weight of an active ingredient consisting essentially of sodium alkene sulphonate and from about 40% to about 60% by weight of the active ingredient of a sodium hydroxy alkane sulphonate, each having an average of from 12 to 18 carbon atoms; and (c) from 2.5 to 6% by weight of sodium sulphate formed as the by-product of a neutralization operation during the production of said sulphate composition, said composition containing substantially no organic cosolvents or added electrolyte, wherein said active ingredient is present as a "G" phase, thereby providing a pourable composition.

* * * * *